United States Patent [19]
Dinh et al.

[11] Patent Number: 6,013,099
[45] Date of Patent: Jan. 11, 2000

[54] MEDICAL DEVICE FOR DELIVERING A WATER-INSOLUBLE THERAPEUTIC SALT OR SUBSTANCE

[75] Inventors: Thomas Q. Dinh; Rodney G. Wolff, both of Minnetonka Beach; Eric P. Berg, Plymouth, all of Minn.

[73] Assignee: Medtronic, Inc., Minneapolis, Minn.

[21] Appl. No.: 09/069,659

[22] Filed: Apr. 29, 1998

[51] Int. Cl.[7] ........................................... A61F 2/06
[52] U.S. Cl. .................................. 623/1; 623/12
[58] Field of Search ........................................... 623/1, 12

[56] References Cited

U.S. PATENT DOCUMENTS

| | | |
|---|---|---|
| 3,105,492 | 10/1963 | Jeckel . |
| 3,425,418 | 2/1969 | Chvapil et al. . |
| 3,451,996 | 6/1969 | Sumyk et al. . |
| 3,523,807 | 8/1970 | Gerendas . |
| 3,549,409 | 12/1970 | Dyck . |
| 3,688,317 | 9/1972 | Kurtz . |
| 4,188,188 | 2/1980 | Willner et al. . |
| 4,229,540 | 10/1980 | Coan . |
| 4,229,838 | 10/1980 | Mano . |
| 4,321,711 | 3/1982 | Mano . |

(List continued on next page.)

FOREIGN PATENT DOCUMENTS

| | | |
|---|---|---|
| 0 366 564 A2 | 5/1990 | European Pat. Off. . |
| WO 86/06729 | 11/1986 | WIPO . |
| WO 89/07932 | 9/1989 | WIPO . |
| WO 91/12779 | 9/1991 | WIPO . |
| WO 94/17108 | 8/1994 | WIPO . |
| WO 94/27612 | 12/1994 | WIPO . |
| WO 97/42911 | 11/1997 | WIPO . |

OTHER PUBLICATIONS

Dyck, "Inorganic Heparin Complexes for the Preparation of Nonthrombogenic Surfaces", *J. Biomed. Mater. Res.*, 6, pp. 115–141 (1972).

Lincoff et al., "Intracoronary Stenting Compared with Conventional Therapy for Abrupt Vessel Closure Complicating Coronary Angioplasty", *J. Am. Coll. Cardiol.*, 21, pp. 866–875, 1993.

Liu et al., "Porous polyurethane vascular prostheses with variable compliances", *J. Biomed. Mater. Res.*, 26, pp. 1489 (1992).

McNair, "Using Hydrogel Polymers for Drug Delivery", *Medical Device Technology*, pp. 16–22, (1996).

"Photolink Surface Modifications Technical Bulletin: Heparin Coatings for Medical Devices", *Brochure from BSI Surface Modification Sciences*, (1994).

William D. Spotnitz et al., "Fibrin Glue from Stored Human Plasma. An Inexpensive and Efficient Method for Local Blood Bank Preparation", *The American Surgeon*, 53, 460–462 (1987).

Van Beusekom et al., "Synthetic polymers as an alternative to metal in stens? In vivo and mechnical behaviour of polyethylene–terephtalate", *Circulation*, 86 (supp. I), pp. I–731, No. 2912, 1992.

K. Whang et al., "A novel method to fabricate bioabsorable scaffolds", *Polymer*, 36:4, 837–842 (1995).

*Primary Examiner*—David H. Willse
*Assistant Examiner*—Suzette J. Jackson
*Attorney, Agent, or Firm*—Daniel W. Latham; Harold R. Patton

[57] ABSTRACT

A device useful for localized delivery of a therapeutic material is provided. The device includes a structure including a porous material; and a water-insoluble salt of a therapeutic material dispersed in the porous material. The water-insoluble salt is formed by contacting an aqueous solution of a therapeutic salt with a heavy metal water-soluble salt dispersed throughout a substantial portion of the porous material. The porous material can be made of a polymer other than fibrin with fibrin incorporated into the pores, which can be the only layer of polymeric material on the medical device (e.g., stent). A new method for preparing a porous polymer material on a medical device.

13 Claims, 5 Drawing Sheets

U.S. PATENT DOCUMENTS

| | | | |
|---|---|---|---|
| 4,540,573 | 9/1985 | Neurath et al. | |
| 4,548,736 | 10/1985 | Muller et al. | |
| 4,612,337 | 9/1986 | Fox, Jr. et al. | 523/113 |
| 4,613,665 | 9/1986 | Larm | |
| 4,623,539 | 11/1986 | Tunc | |
| 4,680,177 | 7/1987 | Gray et al. | |
| 4,733,665 | 3/1988 | Palmaz | |
| 4,768,507 | 9/1988 | Frischell et al. | |
| 4,800,882 | 1/1989 | Gianturco | |
| 4,873,308 | 10/1989 | Coury et al. | |
| 4,886,062 | 12/1989 | Wiktor | |
| 5,010,063 | 4/1991 | Piani et al. | |
| 5,039,529 | 8/1991 | Bergendal et al. | |
| 5,059,166 | 10/1991 | Frischell et al. | |
| 5,061,276 | 10/1991 | Tu et al. | |
| 5,104,860 | 4/1992 | Piani et al. | |
| 5,342,605 | 8/1994 | Illig | |
| 5,352,434 | 10/1994 | Illig et al. | |
| 5,399,318 | 3/1995 | Mancilla et al. | |
| 5,464,650 | 11/1995 | Berg et al. | |
| 5,510,077 | 4/1996 | Dinh et al. | |
| 5,531,735 | 7/1996 | Thompson | |
| 5,541,305 | 7/1996 | Yokota et al. | |
| 5,554,182 | 9/1996 | Dinh et al. | |
| 5,571,166 | 11/1996 | Dinh et al. | |
| 5,591,227 | 1/1997 | Dinh et al. | |
| 5,599,352 | 2/1997 | Dinh et al. | |
| 5,609,629 | 3/1997 | Fearnot et al. | |
| 5,624,411 | 4/1997 | Tuch | |
| 5,679,400 | 10/1997 | Tuch | |
| 5,697,967 | 12/1997 | Dinh et al. | |
| 5,716,981 | 2/1998 | Hunter et al. | |
| 5,776,184 | 7/1998 | Tuch | |
| 5,843,146 | 12/1998 | Slepian et al. | 623/1 |
| 5,848,995 | 12/1998 | Walder | |
| B1 4,733,665 | 1/1994 | Palmaz | |

MEDICAL DEVICE FOR DELIVERING A WATER-INSOLUBLE THERAPEUTIC SALT OR SUBSTANCE

BACKGROUND OF THE INVENTION

This invention relates to a medical device employing a therapeutic substance as a component thereof. For example, in an arterial site treated with percutaneous transluminal coronary angioplasty therapy for obstructive coronary artery disease a therapeutic antithrombogenic substance such as heparin may be included with a device and delivered locally in the coronary artery. Also provided is a method for making a medical device capable of localized application of therapeutic substances. This invention also relates to a medical device, particularly a stent, having a porous polymeric film with fibrin incorporated therein for enhanced biocompatibility, with or without a therapeutic substance as a component thereof.

Medical devices which serve as substitute blood vessels, synthetic and intraocular lenses, electrodes, catheters and the like in and on the body or as extracorporeal devices intended to be connected to the body to assist in surgery or dialysis are well known. For example, intravascular procedures can bring medical devices into contact with the patient's vasculature. In treating a narrowing or constriction of a duct or canal percutaneous transluminal coronary angioplasty (PTCA) is often used with the insertion and inflation of a balloon catheter into a stenotic vessel. Other intravascular invasive therapies include atherectomy (mechanical systems to remove plaque residing inside an artery), laser ablative therapy and the like. However, this use of mechanical repairs can have adverse consequences for the patient. For example, restenosis at the site of a prior invasive coronary artery disease therapy can occur. Restenosis, defined angiographically, is the recurrence of a 50% or greater narrowing of a luminal diameter at the site of a prior coronary artery disease therapy, such as a balloon dilatation in the case of PTCA therapy. In particular, an intra-luminal component of restenosis develops near the end of the healing process initiated by vascular injury, which then contributes to the narrowing of the luminal diameter. This phenomenon is sometimes referred to as "intimal hyperplasia." It is believed that a variety of biologic factors are involved in restenosis, such as the extent of the injury, platelets, inflammatory cells, growth factors, cytokines, endothelial cells, smooth muscle cells, and extracellular matrix production, to name a few.

Attempts to inhibit or diminish restenosis often include additional interventions such as the use of intravascular stents and the intravascular administration of pharmacological therapeutic agents. Examples of stents which have been successfully applied over a PTCA balloon and radially expanded at the same time as the balloon expansion of an affected artery include the stents disclosed in U.S. Pat. No. 4,733,665 issued to Palmaz, U.S. Pat. No. 4,800,882 issued to Gianturco and U.S. Pat. No. 4,886,062 issued to Wiktor. Also, such stents employing therapeutic substances such as glucocorticoids (e.g. dexamethasone, beclamethasone), heparin, hirudin, tocopherol, angiopeptin, aspirin, ACE inhibitors, growth factors, oligonucleotides, and, more generally, antiplatelet agents, anticoagulant agents, antimitotic agents, antioxidants, antimetabolite agents, and anti-inflammatory agents have been considered for their potential to solve the problem of restenosis. Such substances have been incorporated into a solid composite with a polymer in an adherent layer on a stent body with fibrin in a separate adherent layer on the composite to form a two layer system. The fibrin is optionally incorporated into a porous polymer layer in this two layer system.

Another concern with intravascular and extracorporeal procedures is the contact of biomaterials with blood which can trigger the body's hemostatic process. The hemostatic process is normally initiated as the body's response to injury. When a vessel wall is injured, platelets adhere to damaged endothelium or exposed subendothelium. Following adhesion of the platelets, these cells cohere to each other preparatory to aggregation and secretion of their intracellular contents. Simultaneously there is activation, probably by electrostatic charge of the contact factors, of the coagulation cascade. The sequential step-wise interaction of these procoagulant proteins results in the transformation of soluble glycoproteins into insoluble polymers, which after transamidation results in the irreversible solid thrombus.

Immobilization of polysaccharides such as heparin to biomaterials has been used to improve bio- and hemocompatibility of implantable and extracorporeal devices. The mechanism responsible for reduced thrombogenicity of heparinized materials is believed to reside in the ability of heparin to speed up the inactivation of serine proteases (blood coagulation enzymes) by AT-III. In the process, AT-III forms a complex with a well defined pentasaccharide sequence in heparin, undergoing a conformational change and thus enhancing the ability of AT-III to form a covalent bond with the active sites of serine proteases such as thrombin. The formed TAT-complex then releases from the polysaccharide, leaving the heparin molecule behind for a second round of inactivation.

Usually, immobilization of heparin to a biomaterial surface consists of activating the material in such a way that coupling between the biomaterial and functional groups on the heparin (—COOH, —OH, —$NH_2$) can be achieved. For example, Larm presented (in U.S. Pat. No. 4,613,665) a method to activate heparin via a controlled nitrous acid degradation step, resulting in degraded heparin molecules of which a part contains a free terminal aldehyde group. Heparin in this form can be covalently bound to an aminated surface in a reductive amination process. Although the molecule is degraded and as a result shows less catalytic activity in solution, the end point attachment of this type of heparin to a surface results in true anti-thrombogenicity due to the proper presentation of the biomolecule to the surface. In this fashion, the molecule is freely interacting with AT-III and the coagulation enzymes, preventing the generation of thrombi and microemboli.

However, the attachment and delivery of therapeutic substances such as heparin can involve complicated and expensive chemistry. It is therefore an object of the present invention to provide a medical device having a biocompatible, blood-contacting surface with an active therapeutic substance at the surface and a simple, inexpensive method for producing such a surface. It is also an object of the present invention to provide a medical device having a porous material with fibrin incorporated therein, optionally with an active therepeutic substance at the blood-contacting surface. It is also a further object of the present invention to provide a medical device, such as an intravascular stent, having a porous polymeric film adhered to the medical device body with fibrin incorporated therein for enhanced biocompatibility.

SUMMARY OF THE INVENTION

This invention relates to a medical device having a blood-contacting surface with a therapeutic substance thereon. Preferably, the device according to the invention is capable of applying a highly localized therapeutic material into a body lumen to treat or prevent injury. The term "injury" means a trauma, that may be incidental to surgery or other treatment methods including deployment of a stent, or a biologic disease, such as an immune response or cell proliferation caused by the administration of growth factors. In addition, the methods of the invention may be performed in anticipation of "injury" as a prophylactic. A prophylactic treatment is one that is provided in advance of any symptom of injury in order to prevent injury, prevent progression of injury or attenuate any subsequent onset of a symptom of such injury.

In accordance with the invention, a device for delivery of localized therapeutic material includes a structure including a porous material and a plurality of discrete particles of a water-insoluble salt of the therapeutic material dispersed throughout a substantial portion of the porous material. Preferably, the device is capable of being implanted in a body so that the localized therapeutic agent can be delivered in vivo, typically at a site of vascular injury or trauma. More preferably, the porous material is also biocompatible, sufficiently tear-resistant and nonthrombogenic.

The porous material may be a film on at least a portion of the structure or the porous material may be an integral portion of the structure. Preferably, the porous material is selected from the group of a natural hydrogel, a synthetic hydrogel, TEFLON (polytetrafluoroethylene), silicone, polyurethane, polysulfone, cellulose, polyethylene, polypropylene, polyamide, polyester, and a combination of two or more of these materials. Examples of natural hydrogels include fibrin, collagen, elastin, and the like.

Alternatively, the porous material may have fibrin incorporated therein. Although this material preferably has a therapeutic agent also incorporated therein, this is not necessary for enhanced biocompatibility. Thus, in one embodiment, the present invention provides a medical device, preferably, an intravascular stent, that includes a porous polymer film with fibrin incorporated within the pores, optionally with a therapeutic substance also incorporated within the pores.

The therapeutic agent preferably includes an antithrombotic material. More preferably, the antithrombotic material is a heparin or heparin derivative or analog. Also preferably, the insoluble salt of the therapeutic material is one of the silver, barium or calcium salts of the material.

The structure of the device can be adapted for its intended extracorporeal or intravascular purpose in an internal human body site, such as an artery, vein, urethra, other body lumens, cavities, and the like or in an extracorporeal blood pump, blood filter, blood oxygenator or tubing. In one aspect of the invention, the shape is preferably generally cylindrical, and more preferably, the shape is that of a catheter, a stent, or a guide wire.

In another aspect of the invention, an implantable device capable of delivery of a therapeutic material includes a structure comprising a porous material; and a plurality of discrete particles comprising a heavy metal water-soluble salt dispersed throughout a substantial portion of the porous material. Preferably, the heavy metal water-soluble salt is selected from the group of $AgNO_3$, $Ba(NO_3)_2$, $BaCl_2$, and $CaCl_2$. The amount of water-soluble salt dispersed throughout a portion of the porous material determines the total amount of therapeutic material that can be delivered once the device is implanted.

The invention provides methods for manufacturing medical devices. Specifically, the invention provides a method for coating a medical device with a porous polymer (film or coating). The method includes: placing the medical device in a mold; placing a solution of a polymer in the mold with the medical device; wherein the solution of the polymer includes a solvent capable of phase separating from the polymer at a temperature below the freezing point of the solvent; cooling the solution of the polymer in the mold to a temperature below the freezing point of the solvent until a first fraction of particulate material is formed by solidification and phase separation of the solvent from the polymer and is dispersed within solidified polymer; cooling the solution further and at a faster rate than in the first cooling step to form a second fraction of particulate material dispersed within the solidified polymer, wherein the second fraction of particulate material has a smaller particle size than the first fraction; and removing the particulate material from the polymer to form pores therein. Preferably, the medical device is a stent and the solution includes a polyurethane dissolved in dioxane.

The invention also provides methods for making an implantable device which includes therapeutic materials. In one embodiment, a method of the invention includes loading a structure comprising a porous material with a heavy metal water-soluble salt dispersed throughout a substantial portion of the porous material, sterilizing the loaded structure, and packaging for storage and, optionally, delivery of the sterilized loaded structure. Preferably, the method of the invention further includes substantially contemporaneously loading of a water soluble therapeutic material, wherein a water insoluble salt of the therapeutic material is produced throughout a substantial portion of the porous material of the structure. "Substantially contemporaneously," means that the step of loading a water soluble therapeutic material occurs at or near a step of positioning the device proximate to a desired area, i.e., at or near the surgical arena prior to administration to or implantation in, a patient. More preferably, the water insoluble salt of the therapeutic material is dispersed throughout a substantial portion of the porous material.

In another aspect of the invention, a method includes loading a structure comprising a porous material with a heavy metal water-soluble salt dispersed throughout a substantial portion of the porous material; loading a water soluble therapeutic material, wherein a water insoluble salt of the therapeutic material is produced in a substantial portion of the porous material of the structure; and packaging for delivery of the loaded structure.

Thus, the methods for making an implantable device to deliver a therapeutic material and device in vivo, or in an extracorporeal circuit in accordance with the invention, are versatile. A therapeutic material may be loaded onto a structure including a porous material at any number of points between, and including, the point of manufacture and the point of use. As a result of one method, the device can be stored and transported prior to incorporation of the therapeutic material. Thus, the end user can select the therapeutic material to be used from a wider range of therapeutic agents.

DETAILED DESCRIPTION OF PREFERRED EMBODIMENTS

One of the more preferred configurations for a device according to the invention is a stent for use in artery/vascular therapies. The term "stent" refers to any device capable of being delivered by a catheter and which, when placed into contact with a portion of a wall of a lumen to be treated, will also deliver localized therapeutic material at a luminal or blood-contacting portion of the device. A stent typically includes a lumen wall-contacting surface and a lumen-exposed surface. Where the stent is shaped generally cylindrical or tube-like, including a discontinuous tube or ring-like structure, the lumen-wall contacting surface is the surface in close proximity to the lumen wall whereas the lumen-exposed surface is the inner surface of the cylindrical stent. The stent can include polymeric or metallic elements, or combinations thereof, onto which a porous material is applied. For example, a deformable metal wire stent is useful as a stent framework of this invention, such as that described in U.S. Pat. No. 4,886,062 to Wiktor, which discloses preferred methods for making a wire stent. Other metallic stents useful in this invention include those of U.S. Pat. No. 4,733,665 to Palmaz and U.S. Pat. No. 4,800,882 to Gianturco.

Figure 1:
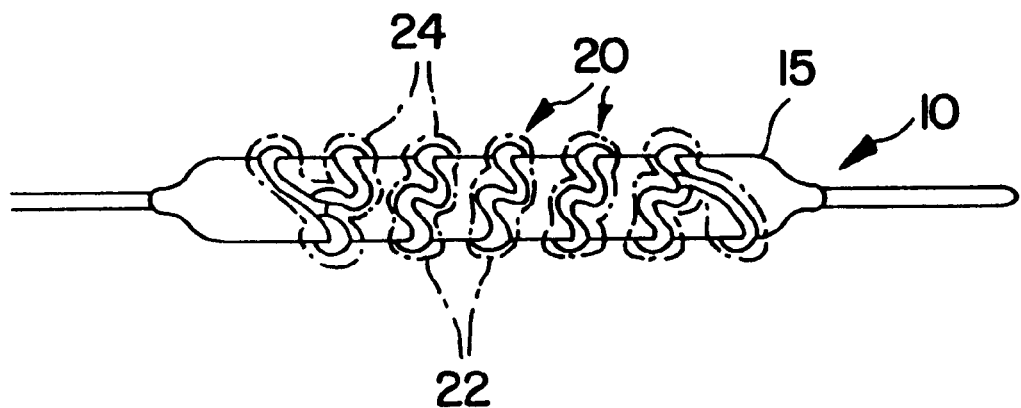
FIG. 1 is an elevational view of one embodiment of a device according to the invention with a balloon catheter as a mode of delivery of the device.

Referring now to FIG. 1, the stent 20 comprises a stent framework 22 and a porous material coating 24. The stent framework 22 is deformable and can be formed from a polymeric material, a metal or a combination thereof. A balloon 15 is positioned in FIG. 1 adjacent the lumen-exposed surface of the stent to facilitate delivery of the stent. The stent 20 can be modified to increase or to decrease the number of wires provided per centimeter in the stent framework 22. Similarly, the number of wire turns per centimeter can also be modified to produce a stiffer or a more flexible stent framework.

Polymeric stents can also be used in this invention. The polymers can be nonbioabsorbable or bioabsorbable in part, or total. Stents of this invention can be completely nonbioabsorbable, totally bioabsorbable or a composite of bioabsorbable polymer and nonabsorbable metal or polymer. For example, another stent suitable for this invention includes the self-expanding stent of resilient polymeric material as disclosed in International Publication No. WO 91/12779.

Nonbioabsorbable polymers can be used as alternatives to metallic stents. The stents of this invention should not substantially induce inflammatory and neointimal responses. Examples of biostable nonabsorbable polymers that have been used for stent construction with or without metallic elements include polyethylene terephthalate (PET), polyurethane urea and silicone (for example, see van Beusekom et al., *Circulation,* 86(supp. I):I-731, 1992 and Lincoff et al., *J. Am. Coll Cardiol.,* 21(supp. 1):335A, 1994. Although the porous material is shown as a coating 24, it is to be understood that, for the purposes of this invention, the porous material can be incorporated into the material of the stent.

Figure 2:
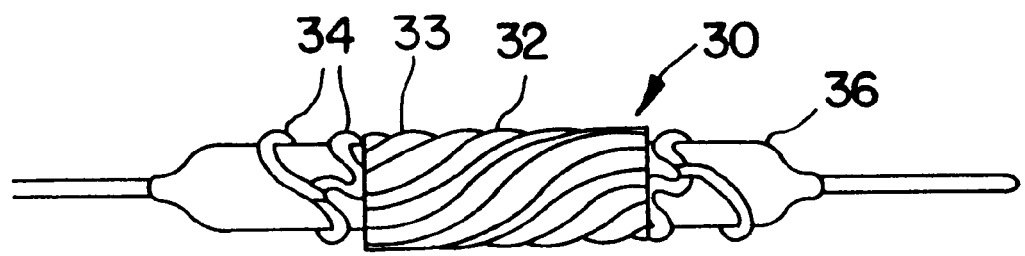
FIG. 2 is an elevational view of another embodiment of a device according to the invention with a balloon catheter as a mode of delivery of the device.

Referring to FIG. 2, an alternative stent 30 is shown. The stent framework 34 is affixed with a film of a porous material 32. This can be accomplished by wrapping the film 32 around the stent framework 34 and securing the film 32 to the framework 34 (i.e., the film is usually sufficiently tacky to adhere itself to the framework but a medical grade adhesive could also be used if needed) so that the film 32 will stay on the balloon 36 and framework 34 until it is delivered to the site of treatment. The film 32 is preferably wrapped over the framework with folds or wrinkles that will allow the stent 30 to be readily expanded into contact with the wall of the lumen to be treated. Alternatively, the film 32 can be molded to the stent framework 34 such that the framework 34 is embedded within the film 32. Preferably, the film 32 is located on a lumen-wall contacting surface 33 of the stent framework 34 such that therapeutic material is substantially locally delivered to a lumen wall, for example, an arterial wall membrane (not shown).

Porous Material

As mentioned above, the device according to the invention is generally a structure including a porous material. In one embodiment, the porous material is a film on at least a portion of the structure. In another embodiment, the porous material is an integral portion of the structure. Preferably, the porous material is biocompatible, and sufficiently tear-resistant and nonthrombogenic. More preferably, the porous material is selected from the group of a natural hydrogel, a synthetic hydrogel, TEFLON (polytetrafluoroethylene), silicone, polyurethane, polysulfone, cellulose, polyethylene, polypropylene, polyamide, polyester, and a combination of two or more of these materials. Examples of natural hydrogels include fibrin, collagen, elastin, and the like. In materials which do not include pores in their usual structural configurations, pores between one micrometer in diameter or as large as 1000 micrometers in diameter can be introduced by conventional means such as by introducing a solvent soluble particulate material into the desired structure and dissolving the particulate material with a solvent. However, no particular pore size is critical to this invention.

In a preferred embodiment, the porous material is made of a polymer other than fibrin (i.e., a non-fibrin porous material) and has fibrin incorporated within the pores. Typically, and preferably, the porous material is in the form of a sheet material of a synthetic biostable polymer. Such synthetic biostable polymers include silicone, polyurethane, polysulfone, cellulose, polyethylene, polypropylene, polyamide, polyester, polytetrafluoroethylene, and combinations thereof.

If the porous material is in the form of a porous sheet or film, it can be made by a variety of methods. These methods can include, for example, forming the films using a solid particulate material that can be substantially removed after the film is formed, thereby forming pores. By using a solid particulate material during film formation, the size of the pores can, to some extent, be controlled by the size of the solid particulate material being used. The particulate material can range from less than about 1 micrometer in diameter to about 1000 micrometers, preferably about 1 micrometer to about 100 micrometers, more preferably about 25 micrometers to about 60 micrometers. For uniformity of pores, the particulate material can be screened through successively finer mesh sieves, e.g., through 100, 170, 270, 325, 400, and 500 mesh analytical grade stainless steel mesh sieves, to produce a desired range of particle sizes.

In one method according to the present invention, a porous polyurethane sheet material (i.e., film) can be made by dissolving a polyether urethane in an organic solvent such as 1-methyl-2-pyrrolidone; mixing into the resulting polyurethane solution a crystalline, particulate material like a salt or sugar that is not soluble in the solvent; casting the solution with particulate material into a thin film; and then applying a second solvent, such as water, to dissolve and remove the particulate material, thereby leaving a porous sheet. Such a method is disclosed, for example, in U.S. Pat. Nos. 5,599,352 and 5,591,227, both issued to Dinh et al. A portion of the particulate material may remain within the film. As a result, it is preferred that the solid particulate material be biocompatible.

Although films for stent bodies according to the present invention can be manufactured separately from the support structure of the stent and attached to the support structure after formation, preferred methods include forming the films directly on the support structure such that the support structure is at least partially, preferably completely, encapsulated by the film. In one such method disclosed in International Publication No. WO 89/07973, a stent is placed on a mandrel. A particulate material is then applied to the mandrel and stent such that it is lightly adhered to the mandrel. The particulate material should be readily soluble in a solvent which will not also dissolve the polymer chosen for the film. For example, crystalline sodium bicarbonate is a water soluble material that can be used as the particulate material. A nonaqueous liquid, preferably a solvent for the polymer film material, can be applied to the mandrel before applying the particulate material in order to retain more of the particulate material on the mandrel. For example, when a polyurethane is to be used for the film material, the solvent 1-methyl-2-pyrrolidinone (NMP) can be used to wet the surface of the mandrel before the application of particulate material. Preferably, the mandrel is completely dusted with the particulate in the portions of the mandrel to be coated with the polymer film. This can be accomplished by dipping the mandrel in NMP, allowing it to drain vertically for a few seconds and then dusting the sodium bicarbonate onto the mandrel while rotating it horizontally until no further bicarbonate particles adhere. Excess particulate material can be removed by gently tapping the mandrel.

Coating with polymer may proceed immediately following application of the particulate material. A polymer is provided in a dilute solution and is applied to the particle-coated stent and mandrel. For example, polyurethane can be dissolved in NMP to make a 10% solution. Gel particles and particulate impurities can be removed from the solution by use of a clinical centrifuge. The polymer solution can be applied by dipping the mandrel into the solution and letting the solvent evaporate. With the solution of polyurethane and NMP, a single dip in the solution can provide a film of adequate thickness. To assist in the formation of communicating passageways through the polymer between the blood-contacting surface and the lumen-contacting surface, additional sodium bicarbonate particles are preferably dusted onto the polymer solution immediately after the dipping operation and before the polymer solution has dried. Excess particulate material can be removed by gently tapping the mandrel. To precipitate and consolidate the polyurethane film on the stent, it can be dipped briefly (about 5 minutes) in water and then rolled gently against a wetted surface, such as a wet paper towel. The stent assembly can then be placed into one or more water baths over an extended period (e.g., 8 hours) to dissolve and remove the sodium bicarbonate. After drying in air at temperatures from about 20° C. to about 50° C., the film then can be trimmed to match the contour of the wire.

In yet another method, a solvent in which the polymer (i.e., a film-forming polymer) is soluble that is capable of phase separating from the polymer at a reduced temperature can be used to prepare a porous polymer film. In this method, the stent or other medical device is placed in a cavity of a mold designed for forming a film around the stent, similar to that disclosed in U.S. Pat. No. 5,510,077 to Dinh et al. A solution of the desired polymer, such as polyurethane, dissolved in a solvent, such as dioxane, is added to the mold. The temperature of the solution is then reduced to a temperature at which the solvent freezes and phase separates from the polymer as it forms a film, thereby forming particulate material (i.e., frozen solvent particles) in situ. Typically, for polyurethane in dioxane, this is a temperature of about −70° C. to about 3° C. The composition is then immersed in an ice cold water bath (at about 3° C.) for a few days to allow the dioxane to dissolve into the ice cold water, thereby forming pores. The number and size of the pores can be controlled by the concentration of the polymer and the freezing temperature. A method similar to this is disclosed in Liu et al., *J. Biomed. Mater. Res.*, 26, 1489 (1992). This method can be improved on by using a two-step freezing process described herein. In a first step, the mixture is cooled slowly to create a first fraction of particulate material (i.e., frozen solvent particles) dispersed within solidified polymer. In a second step, the mixture is cooled further (and more quickly) to create a second fraction of particulate material of smaller size dispersed within solidified polymer. In this way, a wider range of pore sizes can be formed with greater control. This modified method is further described in Example 6.

Therapeutic Material

The therapeutic material used in the present invention could be virtually any therapeutic substance which possesses desirable therapeutic characteristics and which can be provided in both water soluble and water insoluble salts and which have bioactivity as an insoluble salt. For example, antithrombotics, antiplatelet agents, antimitotic agents, antioxidants, antimetabolite agents, anti-inflammatory agents and radioisotopes could be used. "Insoluble salt" or "water insoluble salt" of the therapeutic substance as set forth herein, means that the salt formed has a relatively poor solubility in water such that it will not readily disperse from the pores of the device. In particular, anticoagulant agents such as heparin, heparin derivatives and heparin analogs could be used to prevent the formation of blood clots on the device. Also, water-insoluble radioactive salts such as $AgI^{135}$, $BaS^{35}O_4$, and $(Ca)_3(P^{32}O_4)_2$ could be used for application of radiotherapy to a body lumen or blood.

Preferably, the water-insoluble salt of the therapeutic material is formed by a heavy metal water-soluble salt interacting with an aqueous solution of the therapeutic material. In the present invention, the heavy metal water-soluble salt is dispersed throughout a substantial portion of the porous material. Preferably, the heavy metal water-soluble salt is selected from the group of $AgNO_3$, $Ba(NO_3)_2$, $BaCl_2$, $CaCl_2$, and a mixture thereof. The amount of water-soluble salt dispersed throughout a portion of the porous material determines the ultimate amount of therapeutic material capable of being administered once the device is implanted.

Fibrin and Methods of Incorporation into Porous Polymer

The term "fibrin" herein means naturally occurring polymer of fibrinogen that arises during blood coagulation. It is an insoluble, crosslinked polymer generated by the action of thrombin on fibrinogen. Fibrinogen has three pairs of polypeptide chains (ALPHA 2-BETA 2-GAMMA 2) covalently linked by disulfide bonds with a total molecular weight of about 340,000. Fibrinogen is converted to fibrin through proteolysis by a fibrinogen-coagulating protein, such as thrombin, reptilase, or ancrod.

Methods of making fibrin and forming it into implantable devices are well known in the art. See, for example, U.S. Pat. No. 4,548,736 (Muller et al.) and U.S. Pat. No. 3,523,807 (Gerendas), and European Patent Application 0 366 564. In one method, fibrin is formed by contacting fibrinogen with a fibrinogen-coagulating protein, such as thrombin, reptilase, or ancrod. Preferably, the fibrinogen and fibrinogen-coagulating protein (e.g., thrombin) used to make fibrin is from the same animal or human species as that in which the medical device (e.g., stent) of the present invention will be implanted in order to avoid cross-species immune reactions. The resulting fibrin can also be subjected to heat treatment at about 150° C. for 2 hours in order to reduce or eliminate antigenicity.

Preferably, the fibrinogen used to make the fibrin is a bacteria-free and virus-free fibrinogen such as that described in U.S. Pat. No. 4,540,573 (Neurath et al.). The fibrinogen is preferably used in solution at a concentration of at least about 10 mg/ml, more preferably at least about 26 mg/ml, and no greater than about 50 mg/ml. The pH of the solution is preferably about 5.8 to about 9.0 with an ionic strength of about 0.05 to about 0.45. The fibrinogen solution can include pure fibrinogen, although preferably the solution also includes proteins and enzymes such as albumin, fibronectin, Factor XIII, plasminogen, antiplasmin, Antithrombin HI, and the like. Most preferably, the fibrinogen is cryoprecipitated fibrinogen, which can include hundreds of proteins and enzymes, as disclosed in Spotmitz et al., *The American Surgeon*, 53, 460–462 (1987).

The fibrinogen solution also preferably includes a fibrinogen-coagulating protein, such as thrombin. Alternatively, however, the fibrinogen-coagulating protein solution can be applied after the fibrinogen has been applied. This fibrinogen-coagulating protein solution may or may not include fibinogen. The thrombin is preferably used in solution at a concentration of at least about 1 NIH unit/ml, and no greater than about 120 NIH units/ml. Calcium ions may also be present in the thrombin solution to enhance mechanical properties and biostability of the device. If used, they are preferably present in a concentration of about 0.02 M to about 0.2 M.

Preferably, the coagulating effect of any residual coagulation protein in the fibrin should be neutralized before employing it in a medical device, such as a stent in order to prevent clotting at the fibrin interface with blood after implantation. This can be accomplished, for example, by treating the fibrin with irreversible coagulation inhibitor compounds or heat after polymerization. For example, hirudin or D-phenylalanyl-propylarginine chloromethyl ketone (PPACK) can be used for this purpose. Anticoagulants, such as heparin, can also be added to reduce the possibility of further coagulation.

The porous sheet can then be placed into a fibrinogen solution in order to fill the pores with fibrinogen, followed by application of a solution of thrombin and fibrinogen to the surface of the sheet material to establish a fibrin matrix that occupies both the surface of the sheet and the pores of the sheet. Alternatively, the thrombin can be included within the first fibrinogen solution. If desired, ultrasonics, vacuum, and/or pressure can be used to ensure that the fibrinogen applied to the sheet is received into the pores.

Methods of Making an Implantable Device Having a Therapeutic Substance

Figure 3:
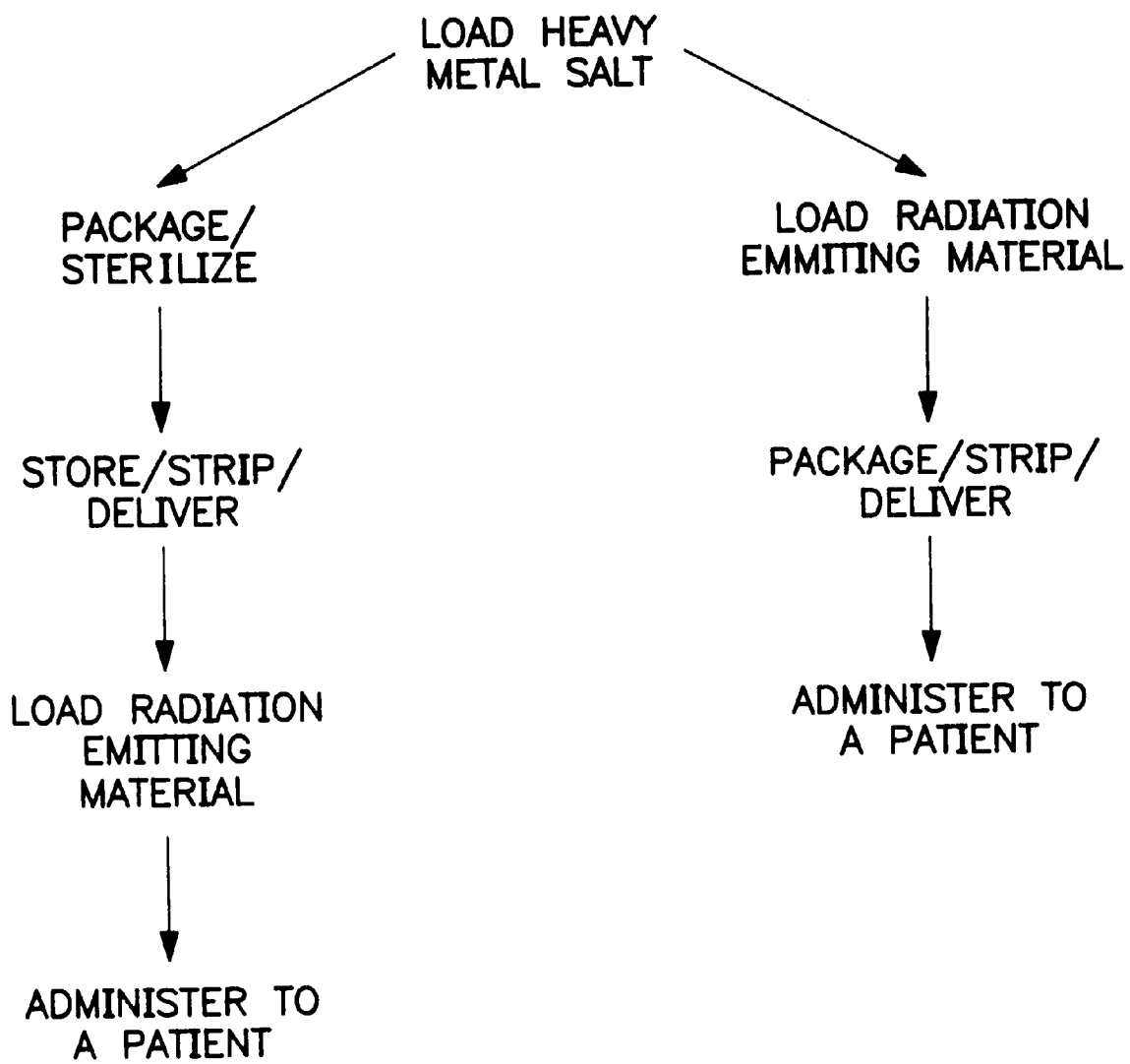
FIG. 3 is a flow diagram schematically illustrating methods according to the invention.

Referring now to FIG. 3, a structure having a porous material is loaded with a heavy metal water-soluble salt. Preferably, this step includes contacting, more preferably immersing, the structure with an aqueous solution of the heavy metal water-soluble salt, as described above. Preferably, the heavy metal water-soluble salt is dispersed throughout a substantial portion of the porous material. This may be assisted by degassing the pores of the structure by such techniques as ultrasound or vacuum degassing. The resulting structure can now be sterilized, packaged and, optionally, stored until use.

In one embodiment of the invention, a sterilized structure is shipped or delivered to the relevant consumer. The structure is substantially contemporaneously loaded with a water soluble therapeutic material. Preferably, the loading of the therapeutic material includes contacting, more preferably immersing, the porous material in an aqueous solution comprising a salt of the therapeutic material, as described above. Again, degassing of the device can help to bring the therapeutic material into the pores. A water-insoluble therapeutic salt is thereby formed within the porous material. Examples of aqueous radioactive salt solutions for radiotherapy include $NaI^{125}$, $K_2S^{35}O_4$, $Na_2S^{35}O_4$, and $Na_3P^{32}O_4$, to name a few.

This method is advantageous in that the structure can be loaded with the therapeutic material in situ, i.e., at or near the point of therapeutic use, typically before administration, preferably implantation, to a patient. This is particularly useful because the device can be stored and transported prior to incorporation of the therapeutic material. This feature has several advantages. For example, the relevant consumer can select the therapeutic material to be used from a wider range of therapeutic materials, e.g., a radioisotope with a certain half-life with certain particle emitting characteristics can be selected. Thus, the therapeutic material selected is not limited to only those supplied with the device but can instead be applied according to the therapy required.

In another aspect of the invention, a sterilized structure is loaded with a therapeutic material. Preferably, the loading of the therapeutic material includes contacting, more preferably immersing, the porous material in an aqueous solution comprising a salt of the therapeutic material, wherein a water-insoluble salt of the therapeutic material is formed within the porous material. Examples of therapeutic salt solutions may be those previously mentioned above. The structure is preferably packaged and can be shipped to the relevant consumer. The structure can now be administered to, preferably implanted into, a patient. Thus, in this embodiment, the structure is loaded with the therapeutic material prior to reaching the point of use, which may be more convenient depending upon the facilities available to the relevant consumer.

EXAMPLES

The following nonlimiting examples will further illustrate the invention. All parts, percentages, ratios, etc. are by weight unless otherwise indicated.

Example 1

The following solutions were used in the procedure:
Solution A: 1–10% aqueous solution of $BaCl_2$
Solution B: 1–10% aqueous solution of $Ba(NO_3)_2$
Solution C: 1–10% aqueous solution of $Na_2S^{35}O_4$ A porcine fibrin stent made according to U.S. Pat. No. 5,510,077 was treated by rehydration in Solution A by immersion for about 5 to about 10 minutes. The stent was removed and excess solution was blotted with absorbent paper. The stent was then dehydrated and sterilized by gamma radiation. Alternatively, Solution B can be used in place of Solution A.

This treated stent was then rehydrated in an aqueous solution of $Na_2S^{35}O_4$ radioisotope having a specific activity of about 10 $\mu$Ci/ml to about 500 $\mu$Ci/ml. A white precipitate of $BaS^{35}O_4$ was observed within the pores of the stent surface. The stent can now be implanted into an artery for localized delivery of $\beta$-radiation or packaged for delivery to the consumer.

Example 2

Figure 4:
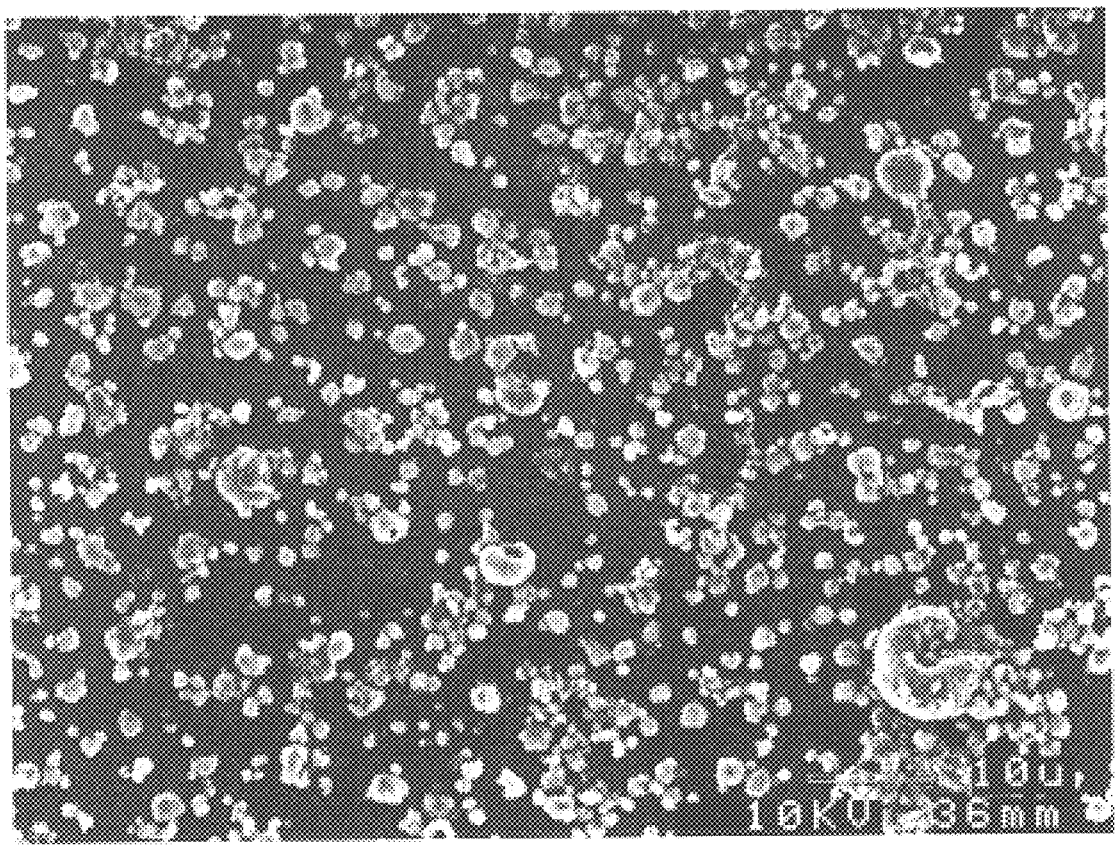
FIG. 4 is a photograph taken from a scanning electron microscope of a surface showing the insoluble therapeutic material according to the invention.
Figure 5B:
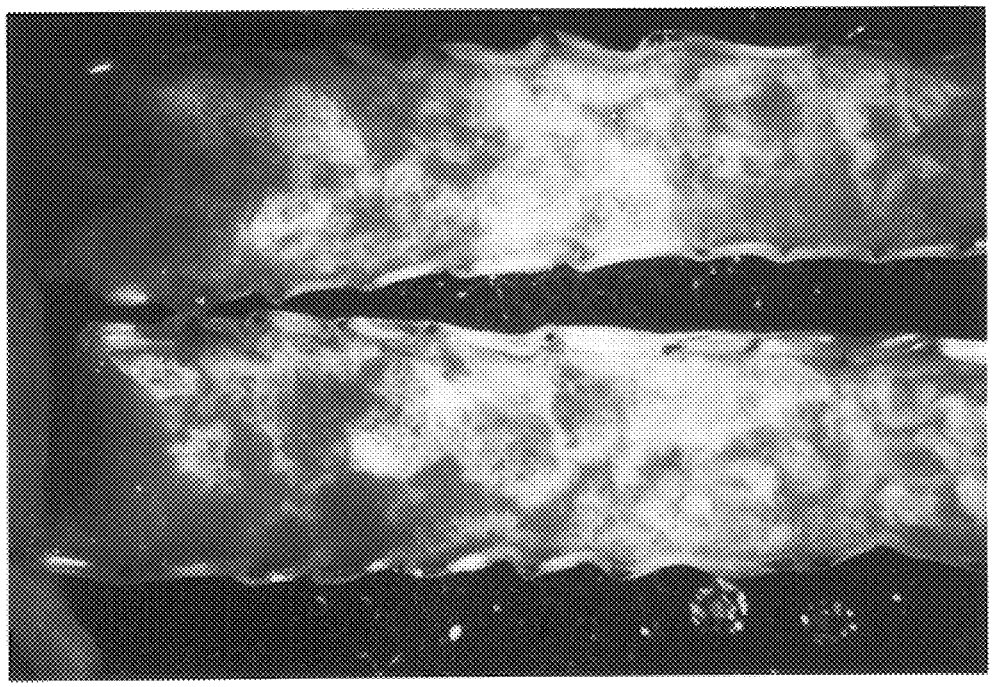
FIGS. 5a and 5b are photographs showing the histological comparison between a stent heparinized according to the present invention (5a) and a control stent (5b)
Figure 5A:
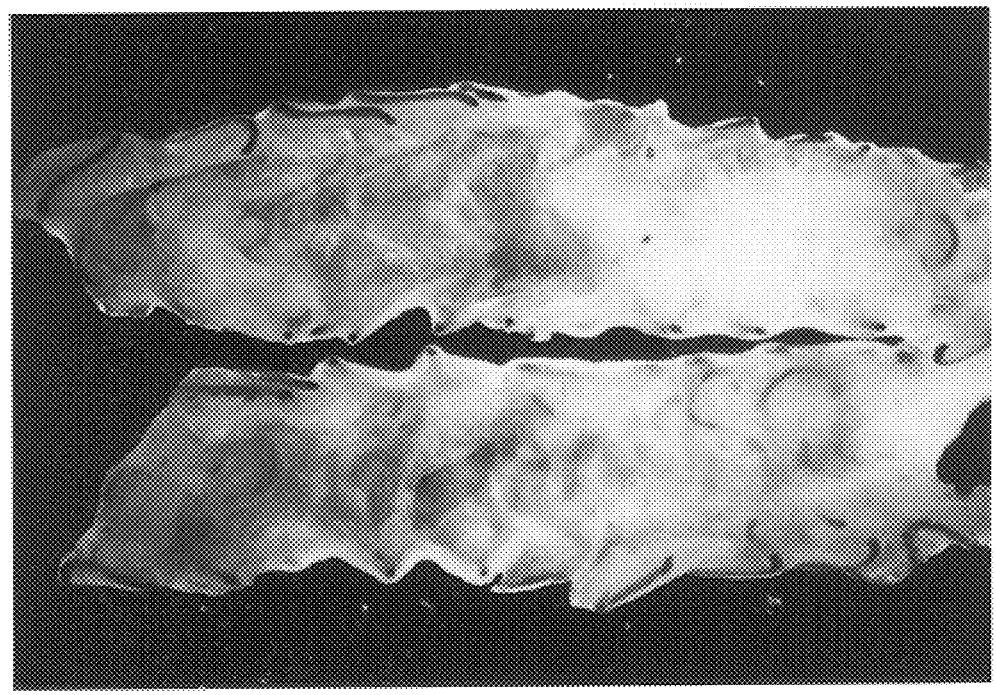

Fibrin stents made according to U.S. Pat. No. 5,510,077 were soaked in a 20% by weight solution of $BaCl_2$ (preferably soaking for about 10 to 30 minutes). The stents were then subjected to degassing by vacuum to remove air from the pores of the fibrin matrix, thus allowing the $BaCl_2$ solution to fill the pores. The stents were dried overnight. The dried stents were placed into a solution of sodium heparinate (preferably soaking in a solution of 1000 U/ml to 20,000 U/ml for 10–20 minutes—most preferably a solution of at least 10,000 U/ml) to allow the $BaCl_2$ in the fibrin matrix to react with the sodium heparinate to form barium heparinate which was precipitated within the fibrin matrix. Scanning electron microscopy (SEM) showed that particulates of barium heparinate on the order of 10 microns (i.e., micrometers) and smaller were trapped within the fibrin matrix (FIG. 4). In vivo evaluation of the barium heparinate stents were carried out using a carotid crush model in pigs with standard fibrin stents as controls. After 24 hours, the stents were compared for flow and were then examined histologically. While flow did not differ in a statistically significant manner between the control stent and the barium heparinate stent, the histological study showed substantially reduced clot formation on the lumenal surface of the barium heparinate stent (FIG. 5a) when compared with the control stent (FIG. 5b).

Example 3

(A) Preparation of porous polyurethane coated stents.

Wiktor type stents were placed over 3.0 mm diameter smooth glass rods and rolled by hand to assure a snug fit. The stent and rod assemblies were dipped in 1-methy-2-pyrrolidinone (NMP) alone at room temperature, allowed to drain vertically for a few seconds, then rotated horizontally while dusting with 400–500 mesh sodium bicarbonate until no further bicarbonate would adhere. After gently tapping the rod assemblies to dislodge lightly adherent bicarbonate, the assemblies were dipped once in a solution of 10 wt % polyurethane in NMP. After draining vertically for a few seconds, the rod and stent assemblies were rotated horizontally while dusting with 400–500 mesh sodium bicarbonate until no further sodium bicarbonate adhered, then gently tapped to dislodge lightly adherent sodium bicarbonate. The assemblies were immersed in water for about 5 minutes, then removed and the coating lightly compacted by gently rolling the coated stent on the mandrel against a wet paper towel. After immersing the stent assemblies in fresh water for at least 8 hours at room temperature the coated stents were removed from their mandrels and immersed in fresh water for 4–8 hours at room temperature. The coated stents were subsequently dried in a forced air oven at 50° C. for about 8 hours and then trimmed of excess coating beyond the stent wires. After passing a visual inspection the porous polyurethane stents were ready for subsequent fibrin impregnation.

(B) Preparation of the composite porous polyurethane-fibrin stent.

The porous polyurethane stents prepared in (A) were suspended in a fibrinogen-thrombin solution. The ratio of fibrinogen to thrombin was predetermined so that the clotting time of fibrinogen was between 5–10 minutes. The fibrinogen-thrombin solution containing the porous polyurethane stents was subjected to vacuum or ultrasonic degassing for about 3–4 minutes. Using either method, the air in the pores of the porous polyurethane stents was driven out and the pores filled with the fibrinogen-thrombin mixture. The stents were then removed from the fibrinogen-thrombin solution and clotting of the fibrinogen in the pores was further carried out for another 10–20 minutes at room temperature after which the stents were incubated in sterile water overnight. After incubation, the stents were dehydrated at room temperature for at least 2 hours. Alternatively, the porous polyurethane fibrin composite stents can be further compressed in glass molds to densify the fibrin prior to dehydration.

Example 4

In Vivo Assessment.

A total of eight prototype stents from example 3 were implanted into 4 pigs for an in vivo assessment. In particular, a single stent was implanted into 2 coronary arteries in each of the 4 pigs. The purpose of this pilot animal study was to asess the deliverability of the composite (fibrin filled porous polyurethane) stents, the acute clinical performance, and to determine the 28-day biocompatibility in terms of tissue response. The pigs were given 325 mg (ASA) per day throughout their course and heparin during the procedure. Stents were crimped onto commercially available PTCA catheters and implanted using standard stent delivery techniques. All eight stents were easily crimped tightly onto the balloons and successfully delivered to the target site through 8Fr or 9Fr guide catheters. Implants were successfully performed in all 3 major coronary arteries (RCA, LAD, LCX). Full expansion was achieved with 6–8 atmospheres pressure. Post-implant angiograms indicated good flow with wide open lumens in all vessels. There were no acute events and the animals recovered without incident. Three of the animals reached their 28-day planned sacrifice date while the fourth pig was humanely sacrificed early at 21 days due to a chronic lung infection (non-cardiac related). All eight stented artery segments were pressure perfusion fixed and sectioned using standard histopathology processing techniques, and subsequently examined histologically. Upon exam all eight stented artery segments were patent (i.e., open)—there were no total occlusions. In 3 of the pigs (6 stents) the lumens were widely patent with mostly thin to very thin amounts of maturing neointima deposited on top of the porous film. In addition, there was absence of or minor amounts of inflammation near the stent material. In the 4th pig (2 stents) a thick neointima compromised the lumen with >60% stenosis and there was significant inflammatory response in the tissue surrounding the stent material. In this particular animal it was noted that the arteries were small and there may have been an overinjury component contributing to the gross vessel response. The pores of the thin film in all these stents were typically filled with native tissue as the exogenous fibrin appears to have been replaced with a cellular infiltrate typical of maturing neointima. There were also some areas of the porous film structure which were still containing the yet-to-be-absorbed exogenous fibrin.

Figure 6:
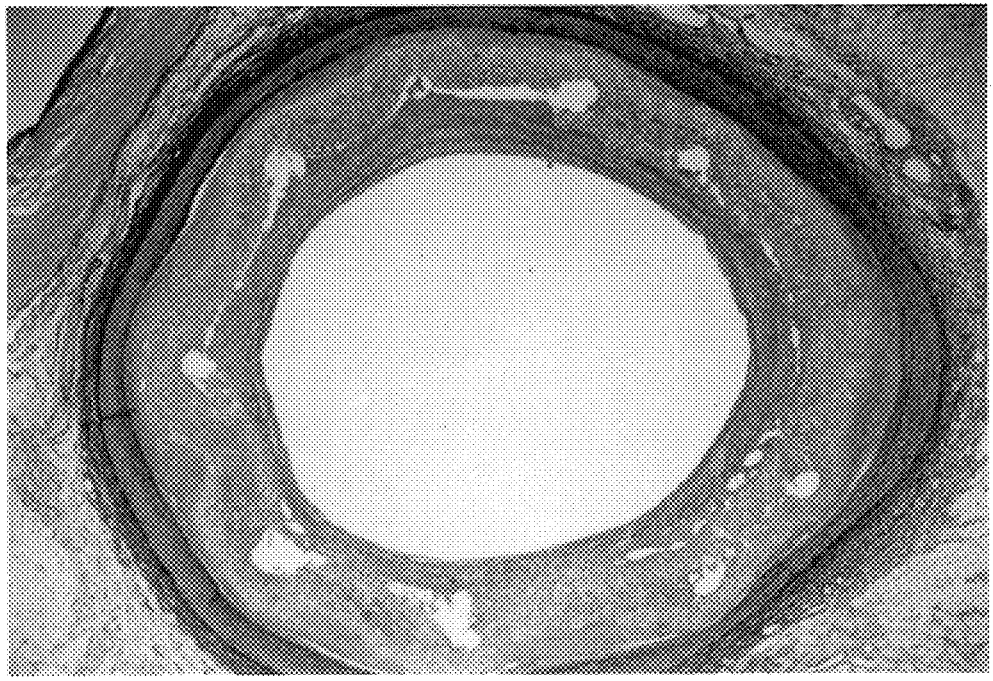
FIGS. 6 and 7 are photographs showing different magnifications of an artery wall with an expanded stent therein having a porous polymer film with fibrin incorporated therein.
Figure 7:
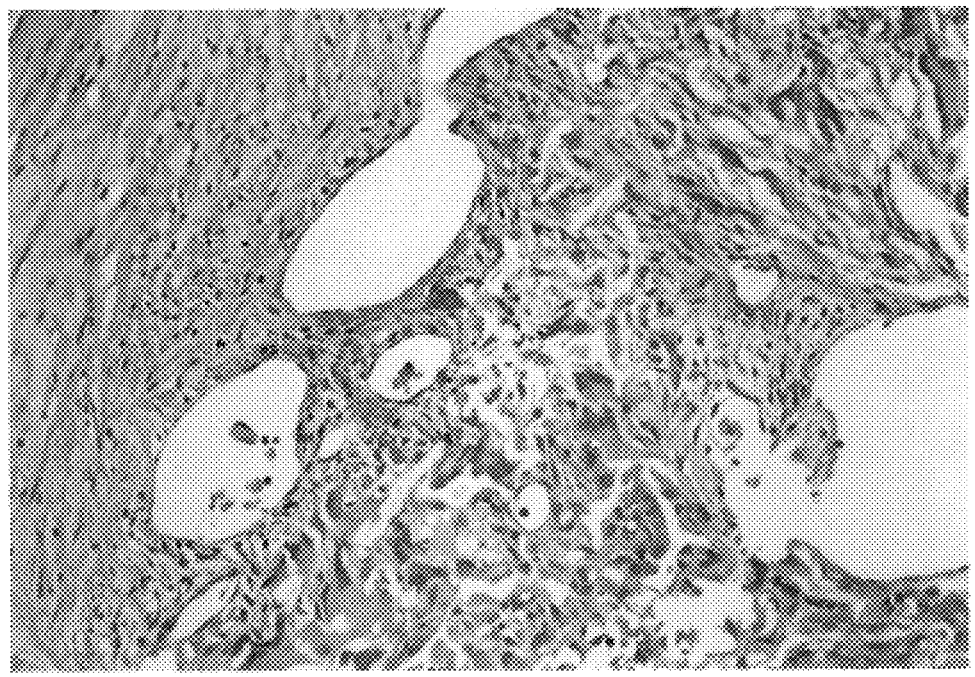

FIGS. 6 and 7 are 28-day examples of elastic van Gieson (EVG) and haematoxylin and eosin (H&E) stains respectively. FIG. 6 indicates the artery wall structure and expanded stent (wire holes plus porous film) with the thin film of neointima on top of the porous film. FIG. 7 is a higher magnification photo of the cellular infiltrate into the porous film with neovascularization taking place at the porous film/neointima interface. Original slide magnifications are 7× and 67×, respectively, for FIGS. 6 and 7. This data indicates that porous polyurethane stents having fibrin incorporated therein can be advantageously used for preventing restenosis without any therapeutic material if so desired.

Example 5

(1) Porous polyurethane impregnated with barium heparinate.

A porous polymer stent prepared according to Example 3(A) was soaked in a 20 wt % solution of barium chloride ($BaCl_2$) for about 10–20 minutes. The stent was then removed and dehydrated for at least 2 hours (preferably overnight). After dehydration, the barium chloride impregnated porous polyurethane stent was placed in a sodium heparin solution with a concentration of at least 10,000 U/ml. The stent was immersed in the heparin solution for about 10–15 minutes during which time the barium chloride reacted with sodium heparin to form barium heparinate. The reaction took place within the pores containing barium chloride and also at the surface of the stent where some of the barium chloride leached out. The barium heparinate, which is not soluble in water, was trapped within the pores of the porous polyurethane stent. The stent was rinsed with sterile water to remove excess, unreacted barium chloride and then dehydrated.

(2) Composite porous polyurethane-fibrin stent impregnated with barium heparinate.

The procedure used was similar to that in (1) above except that the stent described in Example 3(B) was used. After the reaction between barium chloride and sodium heparin was completed, the barium chloride was replaced by barium heparinate that was trapped within the fibrin matrix.

Example 6

Preparation of porous polyurethane coated stent by using a freeze-immersion-precipitation method. Bare stents were cleaned with a mixture of alcohol/water (50:50), and then Freon TE/TF (DuPont) and then dried. After cleaning, the stents were expanded to about 3.1 mm in diameter under clean room conditions. The stents were then individually placed in glass mold cavities. The glass mold cavities have similar configurations as those described in U.S. Pat. No. 5,697,967. A polyurethane solution (6.5 wt % polyurethane in 1,4-dioxan) was injected into the mold cavities using a 3 ml sterile syringe and a 18 Ga sterile needle. After injecting the polymer solution, the glass mold (containing the stents and polymer solution) was place in a refrigerator at 3° C. for 2 hours. Since the freezing temperature of dioxan is at 12° C., the polymer solution frozen slowly thus creating a coarse structure of solvent/polymer. After 2 hours at 3° C., the mold was removed from the refrigerator and transferred to a freezer at –15° C. to –18° C. and kept at this temperature for an additional 1–1.5 hours. The mold was then immersed in an ice cold water bath at 3° C. for 3–4 days to allow the solvent to leach out into the ice cold water. Porous, uniform polyurethane stents were formed after the dioxan completely dissolved into the ice cold water. The mold (and the ice cold water bath) were allowed to warm up slowly to room temperature. The stents were then removed from the glass mold cavities and continued to immerse in fresh water at room temperature for at least one day to remove traces of solvent. The stents were then air dried at room temperature under a clean room flow hood.

The above two-step freezing method was designed to create porous polyurethane stents with desired pore structures and pore sizes. By freezing the polymer solution first at 3° C., large pores (in the order of 50 micrometers or greater) were formed. This was reinforced with smaller pores formed due to additional freezing and crystallization of solvent and polymer at –15° C. to –18° C. The two-step freezing method can create porous polyurethane stents with pore sizes range from 5 to 120 micrometers (with average pore sizes of 50 to 60 micrometers). Pore sizes at 50 to 60 micrometers are desirable for tissue ingrowth.

Fibrin and barium heparinate can also be incorporated in this type of stent using the procedures described in Examples 3 and 5.

The complete disclosures of all patents, patent applications, and publications referenced herein are incorporated herein by reference as if individually incorporated. Various modifications and alterations of this invention will become apparent to those skilled in the art without departing from the scope and spirit of this invention, and it should be understood that this invention is not to be unduly limited to illustrative embodiments set forth herein.

We claim:

1. A medical device having at least one blood-contacting surface comprising:
    a non-fibrin porous material having fibrin incorporated therein; and
    a water-insoluble therapeutic salt dispersed in at least a portion of the porous material.

2. The medical device of claim 1 wherein the non-fibrin porous material comprises a film.

3. The medical device of claim 2 wherein the non-fibrin porous material is selected from the group consisting of silicone, polyurethane, polysulfone, cellulose, polyethylene, polypropylene, polyamide, polyester, polytetrafluoroethylene, and a combination of two or more of these materials.

4. The medical device of claim 2 wherein the water-insoluble salt comprises a salt of an antithrombotic material.

5. The medical device of claim 4 wherein the antithrombotic material is heparin.

6. The medical device of claim 5 wherein the water-insoluble salt is selected from the group consisting of barium, calcium and silver salts of the antithrombotic material.

7. An intravascular stent comprising:
    a generally cylindrical stent body;
    a single layer of a polymeric film comprising a non-fibrin porous polymer with fibrin incorporated therein; and
    a water-insoluble therapeutic salt dispersed in at least a portion of the porous polymeric film.

8. The stent of claim 7 wherein the non-fibrin porous polymer film comprises a material selected from the group of silicone, polyurethane, polysulfone, cellulose, polyethylene, polypropylene, polyamide, polyester, polytetrafluoroethylene, and a combination of two or more of these materials.

9. The stent of claim 8 wherein the non-fibrin porous polymer film comprises a polyurethane.

10. The stent of claim 7 wherein the water-insoluble therapeutic salt is an antithrombotic salt.

11. The stent of claim 10 wherein the antithrombotic salt is a salt of heparin.

12. The stent of claim 11 wherein the water-insoluble heparin salt is selected from the group consisting of silver, barium and calcium salts.

13. The medical device of claim 1 which is in the form of a generally cylindrical stent.

* * * * *